United States Patent [19]
Zitelli et al.

[11] 4,161,121
[45] Jul. 17, 1979

[54] ULTRASONIC IMAGING SYSTEM

[75] Inventors: Louis T. Zitelli, Palo Alto; William L. Beaver, Los Altos Hills, both of Calif.

[73] Assignee: Varian Associates, Inc., Palo Alto, Calif.

[21] Appl. No.: 817,394

[22] Filed: Jul. 20, 1977

Related U.S. Application Data

[63] Continuation of Ser. No. 673,775, Apr. 5, 1976, abandoned.

[51] Int. Cl.² ............................................. G01N 29/00
[52] U.S. Cl. ....................................... 73/626; 128/660
[58] Field of Search ................. 73/610, 611, 612, 619, 73/620, 624, 625, 626, 628, 629, 642; 340/5 R, 5 MP, 9, 1 R; 128/2.05 Z, 2 V

[56] References Cited

U.S. PATENT DOCUMENTS

| | | | |
|---|---|---|---|
| 3,881,164 | 4/1975 | Kossoff | 73/642 |
| 3,881,466 | 5/1975 | Wilcox | 73/626 |
| 3,911,730 | 10/1975 | Niklas | 73/626 |
| 3,936,791 | 2/1976 | Kossoff | 73/626 |

FOREIGN PATENT DOCUMENTS 554178  1/1957  Belgium ....................................... 340/9

*Primary Examiner*—Stephen A. Kreitman
*Attorney, Agent, or Firm*—Stanley Z. Cole; Richard B. Nelson; Peter J. Sgarbossa

[57] ABSTRACT

An electrical-to-acoustic wave transducer contains an array of piezoelectric elements connected to wave-delay circuits to generate a directed acoustic beam and to receive a similarly directed, reflected beam. The distance of a reflecting object is sensed by the time delay of the reflected wave. The apparatus is adapted to sense reflections from both the Fresnel region and the far-field of the array. During the time when reflections from nearby objects in the Fresnel region are received, the effective aperture of the array is reduced by disconnecting elements near its extremities or reducing their gain, producing a narrower beam for improved angular resolution.

20 Claims, 1 Drawing Figure

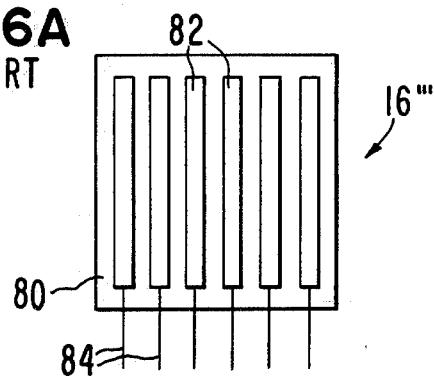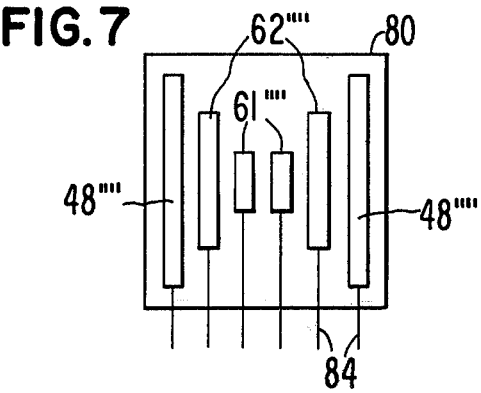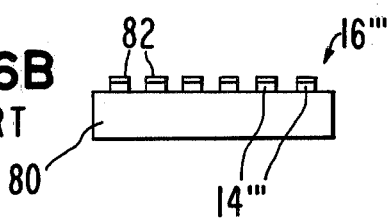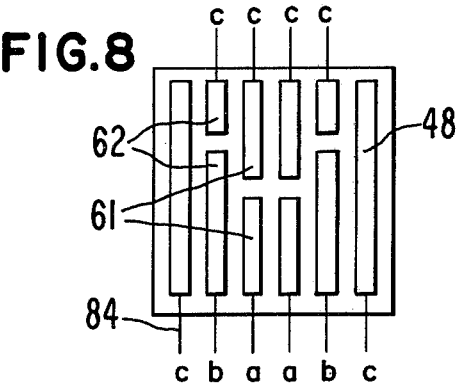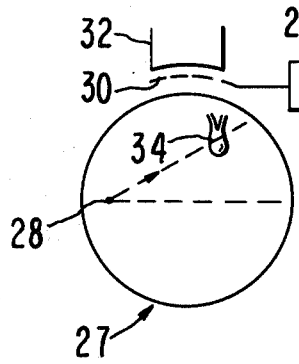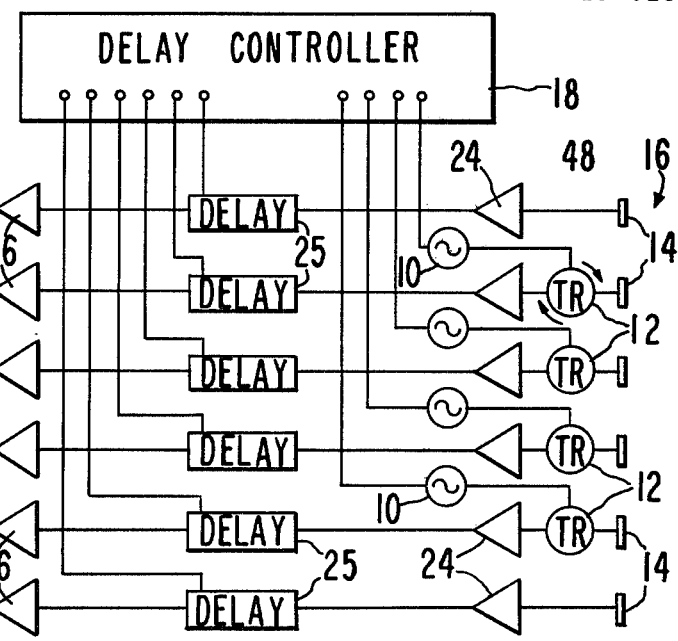

ULTRASONIC IMAGING SYSTEM

This is a continuation of application Ser. No. 673,775 filed 04/05/76, now abandoned.

FIELD OF THE INVENTION

The invention pertains to apparatus for examination of objects by the reflection, scattering or absorption of high-frequency acoustic waves ("ultrasound"). In such apparatus a narrow, pulsed acoustic wave beam is often generated by a piezoelectric transducer having dimensions large compared to the acoustic wavelength. Waves reflected from distant objects in the beam path are received by the same transducer, converted to electrical signals and connected to an electrical sensor. The distance of the reflecting objects from the transducer is measured by the time delay of the reflected signal.

DESCRIPTION OF THE PRIOR ART

High-frequency acoustic waves ("ultrasound") have been widely used to explore solid and liquid bodies. In underwater detection ("sonar"), the objective has been to accurately locate a relatively large object at a great distance. For this purpose a beam of narrow divergence angle in the far-field or Fraunhofer region of the radiator-receiver is needed. Hence, the radiator, an electric-to-acoustic transducer, is made as large as practical compared to the transmitted wavelength, limited by cost, complexity and available area on the vessel.

Aiming the direction of the transmitted and received waves has been generally accomplished by sequential time or phase delays in the electrical signal connected to progressively spaced elements of the transducer.

In ultrasound apparatus for exploring the human body, relatively small transducer arrays have been used because the reflecting objects are fairly close and because, in some cases, such as exploring the chest by a beam passing between ribs, there are physical limits to the usable transducer dimensions. Transducers of the order of 1 centimeter diameter are typical. Since the transducer may be placed quite close to the body, reflections may be received from objects in its Fresnel region close to the transducer as well as from the far-field.

SUMMARY OF THE INVENTION

An objective of the invention is to provide an acoustic wave transducer with optimized beam size throughout both its Fresnel and far-field regions.

A further objective is to provide a transducer whose beam size may be rapidly switched.

A further objective is to provide an apparatus for receiving an acoustic beam wave as reflected by an external object, in which the effective size of the beam may be controlled as a function of the distance of the object.

A further objective is to provide an ultrasonic imaging system in which wave-scattering objects are detected by a transducer whose effective size is made smaller when waves are transmitted to or received from objects in its Fresnel region close to the transducer and is made larger when waves are transmitted to or received from objects farther from the transducer, in either the Fresnel region or the far-field region of the larger transducer, whereby the effective beam size is made as small as possible for both regions.

These objectives are realized by providing the transducer with an array of radiative elements, each connected to an electric circuit through a time delay determinative of the direction of the acoustic beam. For sensing objects in the Fresnel region of the array where the beam size is approximately equal to the physical size of the array, when the objects are close to the transducer outer elements of the array are disconnected from the circuit, forming an effectively smaller beam. The elements may be disconnected during transmitting, receiving, or both. For sensing objects farther away which would be beyond the shortened Fresnel region of the reduced array or in the far-field where the the beam size is inversely proportional to the number of wavelengths across the array, and hence to its physical size, the entire array is connected, at least during transmitting or receiving. The elements may be switched in stepwise fashion or in a continuous sequence.

BRIEF DESCRIPTION OF THE DRAWINGS

FIGS. 6A and 6B show a face and end view of a prior-art transducer array.

FIG. 7 is a face view of an improved transducer array adapted for use with the present invention.

FIG. 8 is a face view of an alternative transducer array.

FIG. 9 is an illustration of time-varying signals of another embodiment.

FIG. 10 is a sketch of the display of the embodiment of FIG. 9.

FIG. 11 is a schematic circuit diagram of another embodiment.

DESCRIPTION OF THE PREFERRED EMBODIMENTS

The invention will be described in terms of an imaging system in which a narrow acoustic wave beam is transmitted by a transducer comprising a spaced array of piezoelectric elements, and waves reflected from distant objects are received by the same array and converted to electrical signals which are in turn eventually converted to a display for indicating the reflecting objects. The invention is however not limited to such a system. Its benefits could be applied to, for example, systems for measuring transmitted or side-scattered acoustic energy with separate transmitter and receiver.

Figure 1:
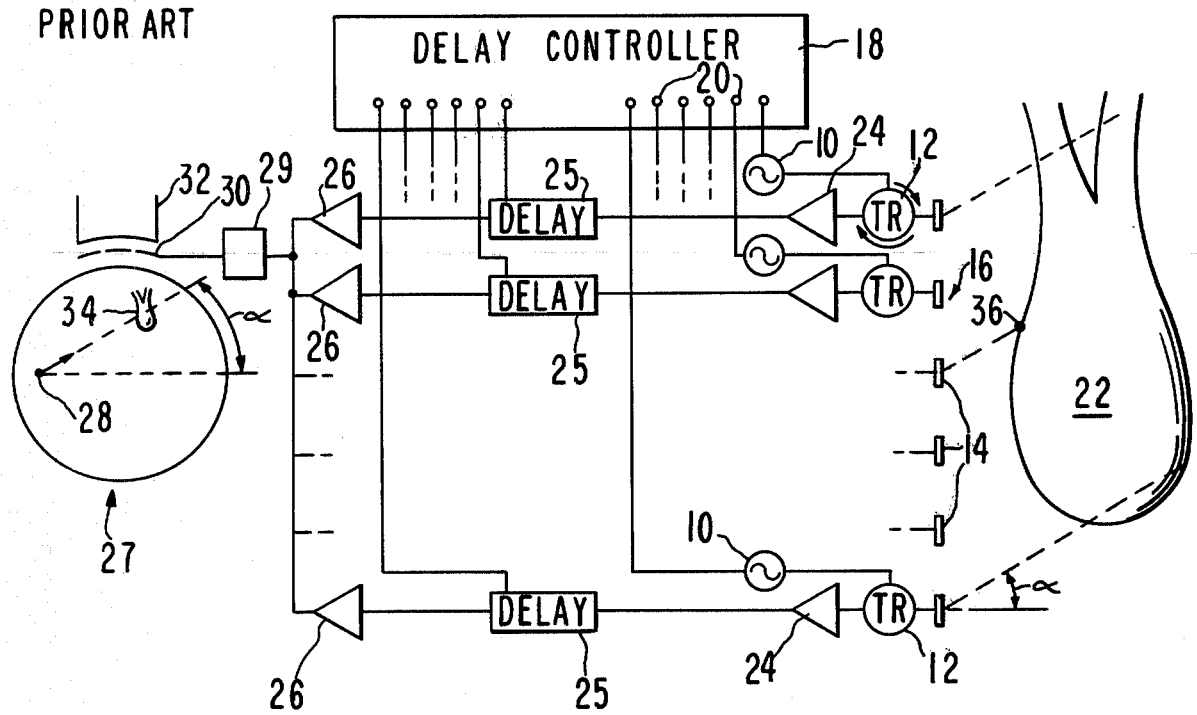
FIG. 1 is a schematic illustration of a prior art ultrasound imaging system with electronic scan.

FIG. 1 shows a schematic illustration of a prior-art ultrasonic imaging sytem. Each of a battery of pulse generators 10 produces a very short electric pulse voltage. This is typically a very short, oscillatory damped wave-train. The pulse is transmitted through a transmit-receive switch 12 which may be a hybrid circuit, a circulator, or an active electronic device such as a diode switch. The pulse is carried to a respective one of the elements 14 of a spaced array 16 of piezoelectric elements. The elements are shown as uniformly spaced and lying in a plane perpendicular to the paper, but other distributions have been used, such as a concave array to focus the beam at some finite distance. If all the elements are driven simultaneously, an acoustic beam will be generated traveling perpendicular to the plane of the array. To change the direction of the beam, each pulser 10 is connected to the delay controller circuit 18 which generates sequential trigger signals on outputs 20 to trigger each pulse generator with an incremental delay time. The signal delay times are determined by delay controller circuit 18, shown schematically. In the uniform array each element in order is excited with a time delay increasing by a uniform amount $\tau$ from the adjacent element. According to well-known wave interference principles, the wave radiated from the array will travel at an angle $\alpha$ from the perpendicular given by the formula $$\sin \alpha = \tau n v / W$$

where:
  n is the number of elements
  W is the height of the array and,
  v is the velocity of the acoustic wave.

Waves reflected from a distant object 22 are converted by the piezoelectric elements 14 to electrical signals, each of which is directed by a transmit-receive (TR) switch 12 through a pre-amplifier 24 to a delay line 25 which introduces the same time delay as was introduced for the transmitter pulse of the particular element. Thus, the array wil have its receiving directivity in the same direction as its beam transmission. Past the delay circuits the received signals go through buffer amplifiers 26 and then are combined. The combined signal is rectified by detector 29 and thence is transmitted to a display or recording device, schematically illustrated is a cathode-ray-tube display 27. The cathode-ray beam is swept by circuitry (not shown) from a starting point 28 representing the position of the transducer. The sweep displacement is in a direction at an angle $\alpha$ from the horizontal equal to the acoustic beam deflection angle. The velocity of sound is approximately constant in the media of interest; thus the time for a wave to be transmitted to a distant object and reflected back to the transducer is directly proportional to the distance of the object. The cathode ray beam is swept at a constant velocity across the tube so the instant when it is at a particular distance from its origin corresponds to the instant at which a reflected wave is received from an external body at a distance proportional to the beam deflection. The received reflection signal is applied to a current-modulating grid 30 in front of the cathode 32 of the cathode-ray tube. Thus the brightness of a spot 34 on the beam trace is determined by the acoustic reflection from an object 36 at the corresponding position in the irradiated space. In operation, delay controller 18 changes the set of signal delays for each pulse so that the acoustic beam is swept over a desired range of angles of scan. Signals from controller 18 are transmitted to the cathode-ray-tube sweep circuitry to generate the corresponding angles of beam deflection. The cathode-ray tube thus displays an image of the entire fan-shaped sector occupied by reflecting objects.

Figure 2:
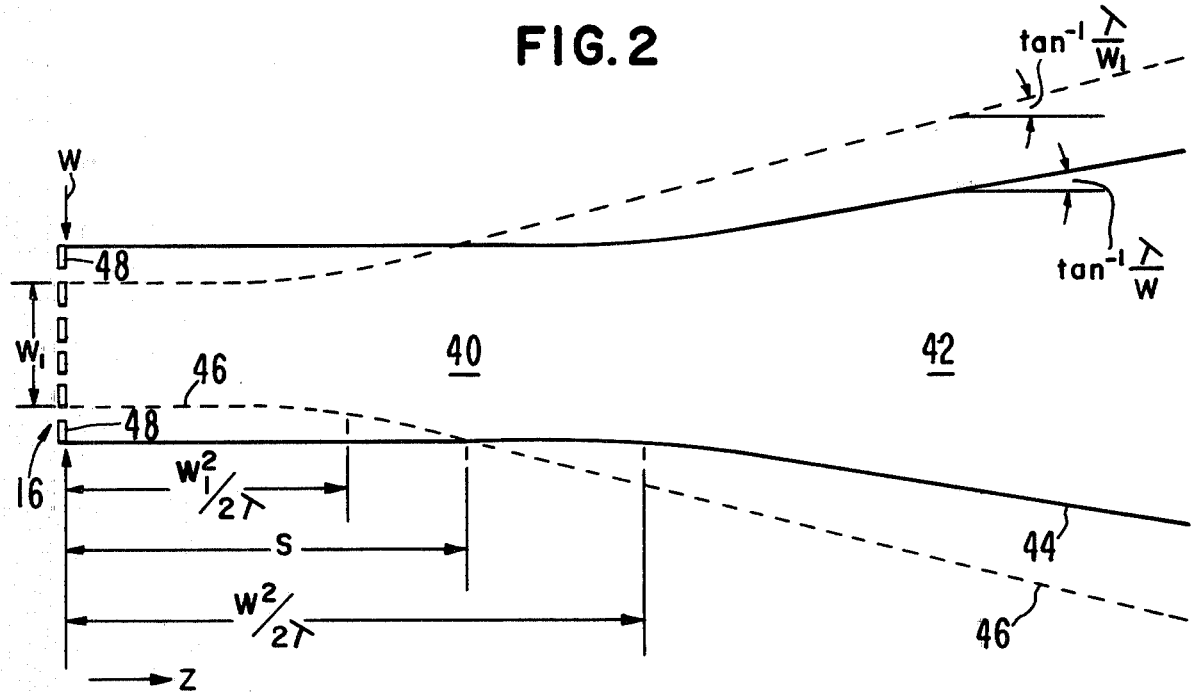
FIG. 2 is a schematic illustration of beam shapes according to the present invention.

FIG. 2 illustrates the outlines of beams produced by wave interference from extended phased radiators. Here the array 16, illustrated as one-dimensional, has a physical width W. If all the elements are driven equally and synchronously, the resulting beam will have a thickness approximately equal to W throughout its so-called Fresnel region 40 extending out to a distance from the array of about $W^2/2\lambda$ where $\lambda$ is the acoustic wavelength. In this Fresnel zone any given cross-section of the beam will have intensity maxima and minima determined by constructive and destructive interference of the radiations from individual elements, but the outline of the beam containing most of its energy will be relatively constant. The region 42 beyond $W^2/2\lambda$ is called the far-field or Fraunhofer region. Here the outline 44 of the beam expands approaching a divergence angle from its center line of $\tan^{-1}(\lambda/W)$ giving a beam width of about $2Z \lambda/W$ when Z, the distance from the array, is very large compared to the size of the array.

In ultrasound imaging systems as used for imaging the human body, reflecting objects may be in either the Fresnel or the far-field region. According to the present invention, when looking at an object in the near portion of the Fresnel region some of the outer elements 48 of transducer array 16 are de-energized. This produces the beam outline 46, shown dotted. The beam in the Fresnel region of the smaller active array is smaller than that from the full-sized array. However, the Fresnel region of the small array is considerably shorter than that of the large array and the far-field beam is correspondingly larger. Thus there is a distance S inside of which the smaller array gives the narrower beam and outside of which the larger array is best. A great utility of this invention arises because, following a transmitted pulse, the reflections from the near regions arrive earlier in time than those from the far regions. Thus, while observing successive reflections of a wave from a single pulse, one can successively connect elements into the array to produce the smallest possible beam size for the particular distance being observed. With the ordinary short-pulse echo-ranging system, the transmitted pulse will normally utilize the entire array to get the smallest possible beam size at great distances to achieve the best lateral resolution and the best signal-to-noise ratio. The elements are then switched only during the receiving time. Other embodiments of the invention may, however, involve reducing the effective size of the array during transmission.

Figure 3:
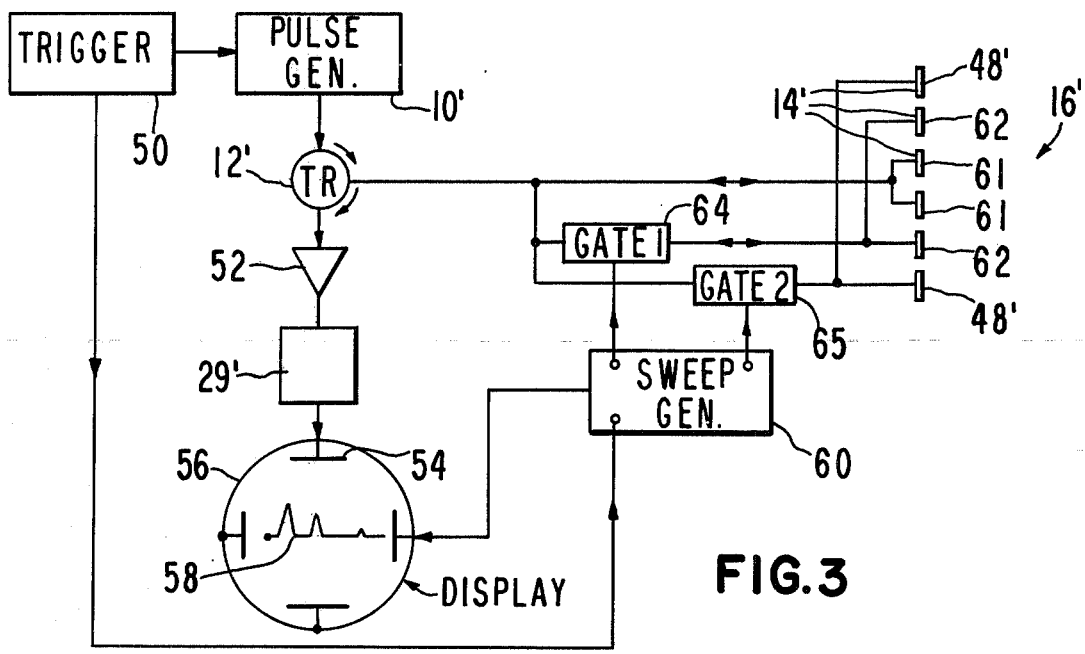
FIG. 3 is a schematic circuit diagram embodying the present invention.

FIG. 3 is a schematic circuit diagram of a simple imaging system embodying the present invention. For simplicity, the transducer array 16' is shown as containing only six elements 14'. It should be realized that in practice much larger numbers of elements would normally be used. Arrays of 32 parallel elements have been found advantageous. To simplify the illustration the circuit of FIG. 3 does not incorporate electronic scanning. A trigger generator 50 produces a periodic train of pulses to time the initiation of the pulse cycle. Each triggger pulse turns on pulse generator 10' to produce a short, oscillatory electric pulse. The pulse is directed by transmit-receive switch 12' simultaneously to the array 16' of piezoelectric elements 14' which generate an acoustic wave perpendicular to their plane. Reflected acoustic waves are reconverted by transducer elements 14' into electric signals which are then combined and transmitted through transmit-receive switch 12' to receiver amplifier 52. The amplified signals are rectified by detector 29' and then applied to the vertical deflection circuit 54 of a CRT display tube 56. The CRT beam 58 is deflected horizontally at a constant velocity by a saw-tooth wave from a sweep generator 60 which is triggered and synchronized by the trigger pulse. As acoustic waves are received the horizontal trace of the cathode ray beam is deflected upward in proportion to the intensity of the waves. The distance of the reflecting object is represented by the horizontal displacement of the reflected signal. Mechanical motion of the transducer may be used to explore in various directions. According to the present invention the central elements 61 of the array are always connected to the electric circuit. The outer elements 62 and 48' are connected through gate circuits 64 and 65, each symmetric pair being connected to a common gate because they are switched synchronously. Immediately after the transmit pulse, when signals are received from very close objects, both sets 62, 48' of outer elements are de-energized "OFF" by gates 64 and 65 in response to timing signals received in predetermined sequence from sweep generator 60. At a later time, when receiving signals from beyond the Fresnel region of the very central elements 61, gate 64 is turned "ON" and the next outer set of elements 62 is re-energized to form an intermediate-sized array. Still later, gate 65 is turned "ON" to re-energize the outermost elements 48' to utilize the full array size for receiving distant signals. Gates 64, 65 may be chosen from many types of electrically controlled devices, such as amplifiers with controlled gain, biased diode switches, electron discharge devices, etc. It may be desirable in some embodiments to have signals from some elements merely reduced in gain instead of completely "OFF".

Figure 4:
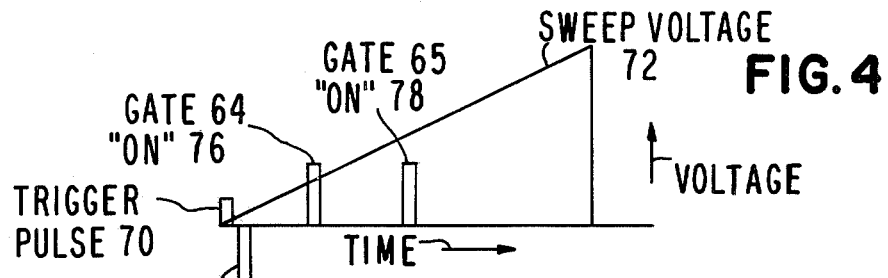
FIG. 4 illustrates the various voltage outputs of the sweep generator in FIG. 3.

FIG. 4 illustrates the various voltage outputs from the sweep generator 60 of FIG. 3. Starting with the trigger pulse 70, a linear sweep 72 for the CRT 56 is generated. Immediately after the trigger pulse, an "OFF" signal 71 is sent to both gates. At later time an "ON" signal 76 goes to gate 64, and still later an "ON" signal 78 goes to gate 65. The sequence is cyclically repeated.

Figure 5:
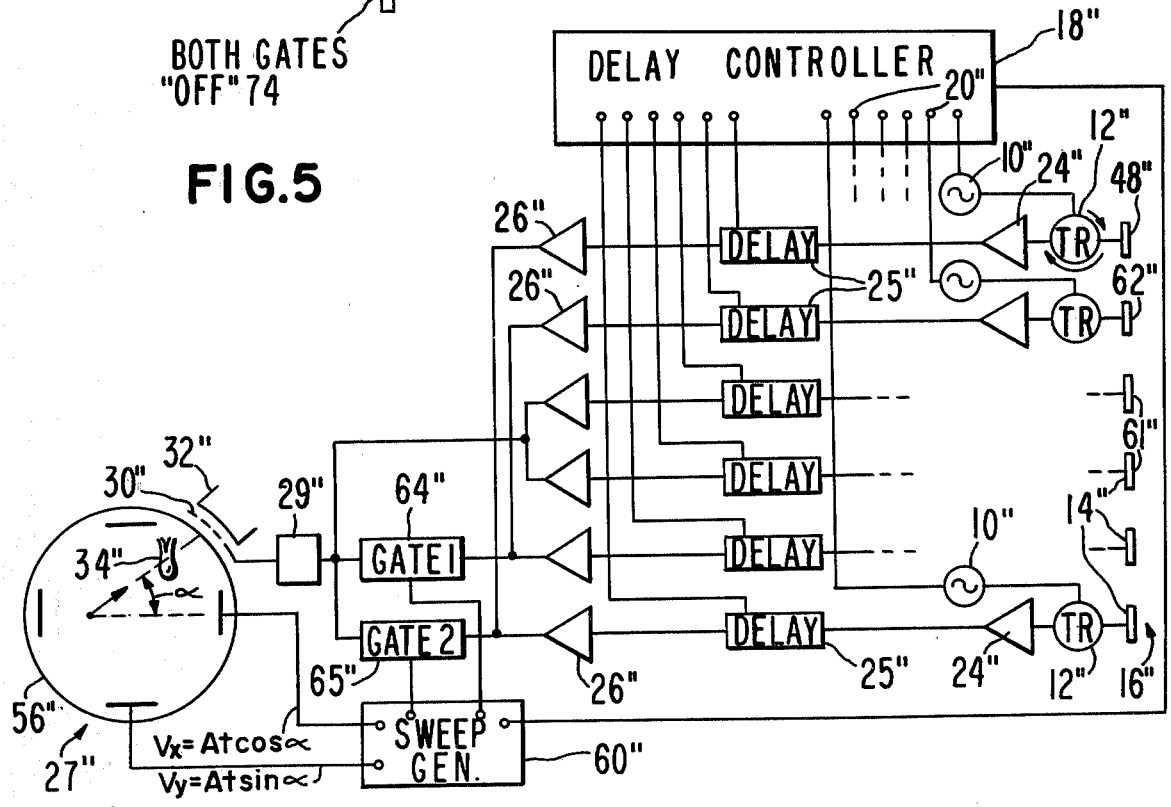
FIG. 5 is a schematic circuit diagram of an imaging system embodying the present invention combined with electronic scanning.

FIG. 5 is a schematic circuit diagram of a more sophisticated embodiment of the invention incorporating an electronic scan as illustrated in FIG. 1 along with the variable beam-width feature illustrated by FIG. 3.

Delay controller 18" is synchronized with a sweep generator 60". Controller 18" generates transmitter trigger pulses on outputs 20" which sequentially fire transmitter pulsers 10". The oscillatory electrical pulses are conducted through TR switches 12" to piezoelectric elements 14" of array 16". Elements 14" are preferably resonant at the oscillatory frequency of pulsers 10", but the Q's of both should be low to produce a short pulse for good range resolution. The angular displacement α of the acoustic beam wave is directed by the time delay between pulsed elements as described above.

Received acoustic echoes are transduced to electric signals by elements 14". They are switched by TR switches 12" through preamplifiers 24" followed by delay lines 25". As described in connection with FIG. 1, the individual delays of lines 25" are controlled by signals from controller 18" to correspond to the individual delays in the transmitted pulse. The delayed signals go through buffer amplifiers 26" and are later combined, rectified by detector 29" and transmitted to the display device 27". The elements 61" at the center of the array 16" and their corresponding delay circuits are connected directly to detector 29". Elements 62" and 48" near the outside of array 16" are connected to detector 29" in symmetric pairs through gate circuits 64", 65". Delay controller 18" is synchronized to vary the respective time delays and resulting beam angles to sweep the beam over a desired angular range during a predetermined number of pulses. A sweep generator 60" switches the gates 64", 65" as described in connection with FIG. 3 and FIG. 4 to regulate the effective beam size in the times following the transmitted pulse to optimize the beam size for each range of reflecting objects. Sweep generator 60" also provides a beam-deflection sweep for the display cathode-ray tube 56". During the echo-receiving time for each pulse, the beam is deflected from an origin at an angle α corresponding to the angle of the acoustic wave for that pulse, in response to angle information received by sweep generator 60" from delay controller 18". This angular cathode ray sweep is generated by coordinated control voltages on the orthogonal deflection elements of the CRT. The vertical deflection receives a signal $V = At \sin \alpha$ and the horizontal deflection receives a signal $V = At \cos \alpha$ where t is the time from the sweep start and A is a scaling constant. In this way, the cathode ray beam is displaced at any instant to a point 34" which is the two-dimensional image point of a corresponding point of reflection of the acoustic beam.

The combined received signals are applied to the control grid 30" of cathode ray tube 56". Control grid 30" modulates the beam current drawn from cathode 32" in response to the amplitude of the received signals. The brightness of the CRT face is thus a two-dimensional map of the acoustic reflections from objects in the fan-shaped sector scanned by the beam.

FIGS. 6A and 6B show the construction of a prior-art transducer adapted for electronic scanning. The array of piezoelectric elements 16''' is affixed to the face of a supporting back plate 80 as of metal. Each element 14''' is covered by a thin metallic electrode 82 to couple the piezoelectric voltage uniformly over its surface. Metallic conductors 84 connect each element to the electric circuitry. In operation, the face of the transducer would normally be acoustically coupled to the body being examined. The transducer array of FIG. 6 is approximately square, so that the beam width is about equal in each dimension. When the array of FIG. 6 is used with the beam-width controlling circuitry of the present invention, disconnecting the outer transducer elements narrows the array dimension, and hence the Fresnel zone beam, only in the direction of the element spacing.

FIG. 7 shows the face of a transducer array adapted to provide optimum beam width in both dimensions. Here the outer elements 48'''' are full length, so that the outline of the array is approximately square. However, the inner elements 61'''', 62'''', which are used alone when the array is switched to a smaller size, are made shorter in their length perpendicular to the array spacing. Thus when the outer elements are switched out, the array is still approximately of square outline.

Some transducer efficiency is, of course, lost by not using the full face area of the transducer array outline, and some distortion of the beam shape occurs due to the non-uniform length of transducer elements.

FIG. 8 shows a more sophisticated transducer which overcomes some of these disadvantages. Here the outer elements 48 extend substantially across the entire face, but each inner element 61, 62 is divided into two sub-elements 61a, 61c and 62b, 62c with individual connecting conductors 84b, 84c and 84a, 84c. When the full array is energized, the two sub-elements of each element are connected together, so the array operates then as an equivalent to the array of FIG. 6. When the outer elements are de-energized to form a smaller array, the corresponding sub-elements of the inner elements are simultaneously disconnected so that the inner elements are then effectively shorter, similar to the results obtained with the array of FIG. 7.

In FIGS. 6, 7 and 8, arrays of only 6 elements are shown to clarify the invention. It should be understood that in practical embodiments, much larger numbers of elements may be used.

The above embodiments have been described and simplified in order to illustrate the invention. It will be readily apparent to those skilled in the art that many other modifications of the invention may be made within its true scope.

For example, the array may be switched between large and small size between successive pulses. A simple case is illustrated by FIGS. 9 and 10. FIG. 9 shows the time sequence of operation. On odd numbered pulses only, the small array of inner transducer elements 61 is energized to transmit and receive. During reception of odd pulses, display 86 is blanked out and after time $t_s$ when the two alternating beams are of approximately equal size, corresponding to distance S of FIG. 2. Thus, with a cathode-ray-tube display such as 27″ of FIG. 5, here illustrated by FIG. 10, signals from this pulse will appear only within radius $\Sigma$ corresponding to distance S and time $t_s$.

On even numbered pulses, all elements of array 16 are energized for transmitting and receiving. The received signal is blanked out from the time of the pulse up to $t_s$. Display signals thus appear only outside radius $\Sigma$. The image retention of the eye or a camera easily combines the two alternately presented parts of the image.

A still simpler embodiment of the invention is illustrated by FIG. 11. Here pulsers 10 and TR switches 12 driving outer array elements 48 are removed or not energized. Thus all pulses are transmitted from the small array. When receiving echoes the entire array is always energized. No gate circuits are required. This embodiment takes advantage of the fact that the effective resolution is largely determined by the smaller of either the transmitting beam width or the receiving beam width. Thus, if one transmits with either beam and receives with the other, the effective resolution at any distance is automatically the smaller of the two beams. Of course the relation of transmitting and receiving elements of FIG. 11 can be reversed, transmitting with the large array and disconnecting the outer elements from the receiver. By well-known reciprocity theorems the results are equivalent. It should be noted that the simple circuit of FIG. 11 will have poorer signal-to-noise ratio from the far-field than the more complex circuits described previously.

Another possible embodiment of the invention is in a linear-scan array. The apparatus includes a very long, linear array of transducer elements. For each pulse, a selected contiguous group of elements are energized. Elements are sequentially added to one end of the group and subtracted from the other so that the energized area progresses down the length of the array. Energized elements of each pulse are connected in the same phase so the beam is perpendicular to the array while it scans sideways across the array. The de-energizing of outer elements of the active group can be done by any of the methods previously described for conventional arrays.

The above embodiments are to illustrate the invention, many other embodiments and features will be apparent to those skilled in the art. The invention is intended to be limited only by the following claims and their legal equivalents.

We claim:

1. A phased array acoustic beam scanning apparatus comprising:
    an array of transducer elements for interchanging energy with an acoustic beam, said elements being spaced side-by-side in a first direction;
    means for applying repetitive electric pulses to form said acoustic beam, said means including delay circuit means for sweeping said beam over a desired angular range in a plane transverse to said transducers and including said first direction; and
    means synchronized with said pulses for activating said elements to receive reflections of said beam and convert same to analogous electrical signals, said means de-energizing at least a symmetric outer pair of elements of said array to reduce the extent of the active elements of said array during the time period in which near field reflected acoustic information arrives at said array, whereby an effectively smaller array is presented during detection of said near field reflected information.

2. A method of providing improved resolution of ultrasonic images comprising the steps of: electrically exciting an array of piezoelectric elements thereby producing an acoustic wave, sensing electrical signals generated by said array of piezoelectric elements in response to reflections of said acoustic wave from material at a distance from said array, de-energizing at least one element of said array during the time reflections from the near field arrive at said array, and re-energizing said one element during the time reflections from the far field arrive at said array.

3. The method of claim 2 in which said step of de-energizing includes de-energizing one or more outer symmetric pairs of elements of said array, and said step of re-energizing includes re-energizing said one or more outer symmetric pairs of elements.

4. In combination with an array of transducer elements adapted to interchange energy with an acoustic wave beam, said elements being spaced in a first direction transverse to said beam, means for applying repetitive electric pulses to a plurality of said elements to generate acoustic pulses to form said beam, and means synchronized with said pulses for activating said elements to receive reflections of said beam and convert same to analogous electrical signals, the improvement in which:
    said means for activating said elements de-energizes at least one of the elements of said array to reduce the extent of the active elements of said array during the time period in which near field reflected acoustic information arrives at said array, thereby reducing the width of said beam in said first direction for improved probing of material close to said array.

5. In combination with an array of transducer elements adapted to interchange energy with an acoustic wave beam, said elements being spaced in a first direction transverse to said beam, means for applying repetitive electric pulses to a plurality of said elements to generate acoustic pulses to form said beam, and means synchronized with said pulses for activating said elements to receive reflections of said beam and convert same to analogous electrical signals, the improvement in which:
    said means for activating said elements de-energizes at least one of the elements of said array during the time period in which near field reflected acoustic information arrives at said array, thereby reducing the width of said beam in said first direction for improved probing of material close to said array, and in which said means for activating said elements re-energizes said one element during the time period when far field reflected acoustic information arrives at said array.

6. The apparatus of claim 5, in which said means for activating said elements de-energizes one or more outer symmetric pairs of the elements of said array.

7. In an acoustic wave probing apparatus:
a side-by-side array of transducer elements adaptable to interchange energy with an acoustic wave beam;
means for generating repetitive electric pulses;
means for applying first ones of said electric pulses to an inner subset of said transducer array to generate an acoustic wave beam and for applying second ones of said electric pulses to the complete array to generate an acoustic wave beam;
means for sensing electric signals generated in response to reflections of said acoustic wave beam by said inner subset subsequent to said first ones of said electric pulses, and for sensing electric signals generated by the complete array subsequent to said second pulses,
whereby resolution for reflected acoustic information from the near field is preferentially enhanced during said first pulses, while resolution for reflected acoustic information from the far field is enhanced during said second pulses.

8. The apparatus of claim 7 in which said means for sensing electric signals includes means for displaying said signals in response to the sensing thereof during a first predetermined time immediately after said first pulses.

9. The apparatus of claim 7 in which said means for sensing electric signals includes means for displaying said signals in response to the sensing thereof during
a. a first predetermined time after said first pulses sufficient to allow near field reflected acoustic information to return to said inner subset, and
b. a second predetermined time after said second pulses, approximating the time when far field reflected acoustic information begins to return to said array.

10. The apparatus of claim 9, in which said first and second predetermined times are the same.

11. An improved method of interrogating an object with an array of ultrasonic transducers, comprising the steps of:
transmitting an acoustic wave into said object by electrically exciting one of two sets of transducers, one set consisting of a plurality of said transducers, the other set consisting of an inner subset of said plurality;
and receiving reflections of said wave from within said object with the other of said set of transducers
whereby the reception of the reflected acoustic information from both the regions near the array, as well as more distant from the array is improved.

12. A method as in claim 11 wherein said plurality of transducers comprises said entire array.

13. A method as in claim 11 wherein said plurality of transducers includes only a portion of the total of said transducers in said array, and are sequentially employed.

14. A method as in claim 11 which further includes the step of providing repetitive electric pulses, and in which said transmitting is performed on first ones of said electrical pulses with one of said sets of transducers, and on second ones of said pulses with the other of said sets.

15. An improved method of interrogating an object with an array of ultrasonic transducers, comprising the steps of:
transmitting an acoustic wave into said object by electrically exciting an inner subset of said plurality of transducers;
and receiving reflections of said wave from within said object with said entire plurality;
whereby the reception of the reflected acoustic information from both the regions near the array, as well as more distant from the array is improved.

16. An improved method of interrogating an object with an array of ultrasonic transducers, comprising the steps of:
transmitting an acoustic wave into said object by electrically exciting a plurality of transducers;
and receiving reflections of said wave from within said object with said inner subset of said plurality of transducers,
whereby the reception of the reflected acoustic information from both the regions near the array, as well as more distant from the array is improved.

17. In combination with a side-by-side array of acoustic transducers for interrogating an object of interest:
means for electrically exciting a plurality of said transducers to transmit an acoustic wave into said object;
means for activating said transducers to receive reflections of said acoustic wave and convert same to analogous electrical signals, said means actuating at least one inner subset of said transducers of said array at a time earlier than that of any of the remaining transducers of said array;
whereby said reflections emanating from regions of said material relatively near said array are sensed by said inner subset, while reflections emanating from relatively distant regions are sensed by at least some elements of the remaining array, for optimal treatment of both near and far field reflected acoustic information.

18. The combination of claim 17 in which said inner subset includes at least an innermost subset and next outermost subset, and said means for activating transducers to receive said reflection includes means for sequentially activating first said innermost subset, and then said outermost subset along with said innermost subset.

19. The combination of claim 17, in which said means actuating said transducers to receive reflections actuates first said inner subset, then all other transducers of said array.

20. The combination of claim 17, in which said means for exciting said transducers to transmit excites said entire array.

* * * * *